(12) United States Patent
Crowley et al.

(10) Patent No.: US 7,991,455 B2
(45) Date of Patent: *Aug. 2, 2011

(54) SYSTEMS AND METHODS FOR DYNAMIC OPTICAL IMAGING

(75) Inventors: Robert J. Crowley, Sudbury, MA (US); Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 506 days.

This patent is subject to a terminal disclaimer.

(21) Appl. No.: 12/103,599

(22) Filed: Apr. 15, 2008

(65) Prior Publication Data

US 2008/0275304 A1 Nov. 6, 2008

Related U.S. Application Data

(63) Continuation of application No. 10/444,171, filed on May 22, 2003, now Pat. No. 7,376,455.

(51) Int. Cl.
*A61B 6/00* (2006.01)
(52) U.S. Cl. .......... 600/473; 600/475; 600/476
(58) Field of Classification Search .......... 600/309–344, 600/407, 408, 473–480; 606/1–19
See application file for complete search history.

(56) References Cited

U.S. PATENT DOCUMENTS

| | | | | |
|---|---|---|---|---|
| 4,175,545 | A | * | 11/1979 | Termanini ............... 600/479 |
| 4,204,528 | A | * | 5/1980 | Termanini ............... 600/109 |
| 4,339,775 | A | * | 7/1982 | Lemke et al. ............ 386/200 |
| 4,923,462 | A | * | 5/1990 | Stevens ................... 606/159 |
| 5,290,275 | A | * | 3/1994 | Kittrell et al. .............. 606/15 |
| 5,496,305 | A | * | 3/1996 | Kittrell et al. .............. 606/15 |
| 5,569,276 | A | * | 10/1996 | Jang et al. ............... 606/159 |
| 5,602,394 | A | * | 2/1997 | Dombrowski et al. .. 250/339.02 |
| 5,895,397 | A | * | 4/1999 | Jang et al. ............... 606/159 |
| 5,943,133 | A | | 8/1999 | Zeylikovich et al. |
| 5,949,074 | A | * | 9/1999 | Dombrowski et al. .. 250/339.02 |

(Continued)

FOREIGN PATENT DOCUMENTS

EP 1090582 A1 4/2001

(Continued)

OTHER PUBLICATIONS

Yasuno, Y., et al., Spectral interferometric optical coherence tomography with nonlinear β-barium borate time gating, Optics Letters vol. 27 No. 6 Mar. 15, 2002, pp. 403-405.

(Continued)

*Primary Examiner* — Sanjay Cattungal
(74) *Attorney, Agent, or Firm* — Frommer Lawrence & Haug LLP; Bruce E. Black

(57) ABSTRACT

A medical system includes a catheter having an elongated tubular member and an inner core slideably received within the elongated member. The inner core includes an imager on a distal end and is coupled with a control system and an imaging system. The inner core is configured to scan the interior of a lumen by radially rotating around a center axis and axially translating along the center axis while within the elongated member. The medical system is configured to dynamically image a body lumen at a high speed in order to allow for optical imaging in a safe manner without long durations of blood sequestration and displacement. The medical system is configured to obtain three dimensional images of the body lumen with as little as one dimensional scanning of the lumen. Images of the lumen can be stored and viewed at a desired rate after scanning.

27 Claims, 3 Drawing Sheets

U.S. PATENT DOCUMENTS

| | | | |
|---|---|---|---|
| 6,002,480 A * | 12/1999 | Izatt et al. | 356/479 |
| 6,123,923 A * | 9/2000 | Unger et al. | 424/9.52 |
| 6,134,003 A * | 10/2000 | Tearney et al. | 356/479 |
| 6,437,867 B2 * | 8/2002 | Zeylikovich et al. | 356/497 |
| 6,445,939 B1 * | 9/2002 | Swanson et al. | 600/342 |
| 6,445,944 B1 | 9/2002 | Ostrovsky | |
| 6,471,659 B2 * | 10/2002 | Eggers et al. | 600/564 |
| 6,501,551 B1 * | 12/2002 | Tearney et al. | 356/477 |
| 6,615,072 B1 * | 9/2003 | Izatt et al. | 600/478 |
| 6,679,269 B2 * | 1/2004 | Swanson | 128/898 |
| 6,687,010 B1 * | 2/2004 | Horii et al. | 356/479 |
| 6,762,839 B2 * | 7/2004 | Zeylikovich et al. | 356/397 |
| 6,785,400 B1 * | 8/2004 | Farina | 382/100 |
| 6,846,985 B2 * | 1/2005 | Wang et al. | 174/391 |
| 6,847,454 B2 * | 1/2005 | Crowley et al. | 356/479 |
| 6,884,407 B1 * | 4/2005 | Unger | 424/9.52 |
| 6,973,162 B2 * | 12/2005 | Block et al. | 378/63 |
| 7,006,231 B2 * | 2/2006 | Ostrovsky et al. | 356/479 |
| 7,672,478 B2 * | 3/2010 | Farina | 382/100 |
| 2002/0091325 A1 | 7/2002 | Ostrovsky | |
| 2003/0004412 A1 | 1/2003 | Izatt et al. | |
| 2003/0020922 A1 | 1/2003 | Crowley et al. | |
| 2003/0028100 A1 * | 2/2003 | Tearney et al. | 600/431 |
| 2004/0009406 A1 * | 1/2004 | Hesselink et al. | 430/1 |
| 2006/0093276 A1 * | 5/2006 | Bouma et al. | 385/72 |

FOREIGN PATENT DOCUMENTS

| | | |
|---|---|---|
| JP | 11056786 A | 3/1999 |
| JP | 2000262461 A | 9/2000 |
| JP | 2001507251 | 6/2001 |
| JP | 2001356095 A | 12/2001 |
| JP | 2003035660 A | 2/2003 |
| WO | 0042906 A2 | 7/2000 |

OTHER PUBLICATIONS

Tripathi, R. et al., Spectral shaping for non-Gaussian source spectra in optical coherence tomography, Optics Letters vol. 27, No. 6 Mar. 15, 2002, pp. 406-408.

Fujimoto J. G. et al, "Femtosecond Optical Ranging in Biological Systems," Opt. Lett. (USA), Optics Letters, Mar. 1986, USA, vol. 11, No. 3, Mar. 1986, pp. 150-152, ISSN: 0145-9592, p. 150.

* cited by examiner

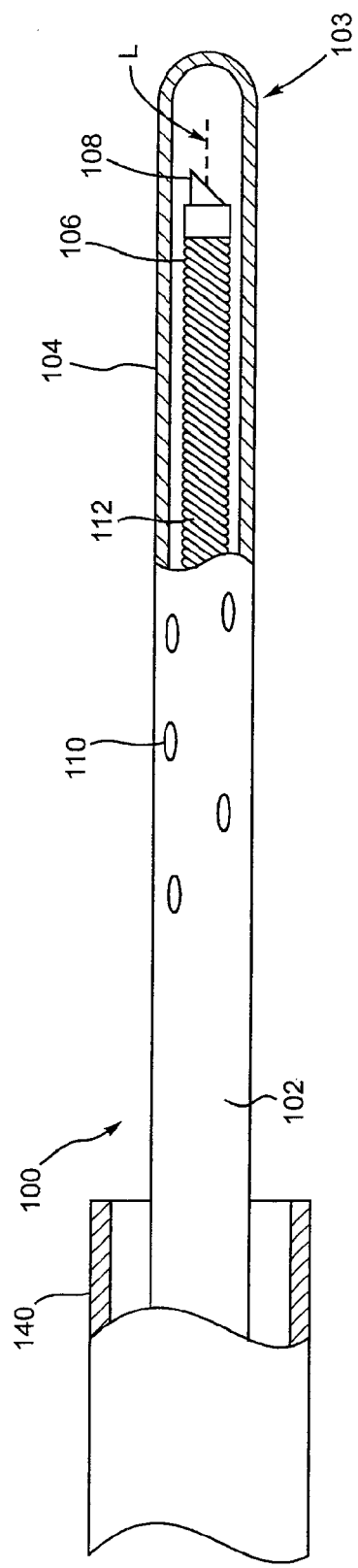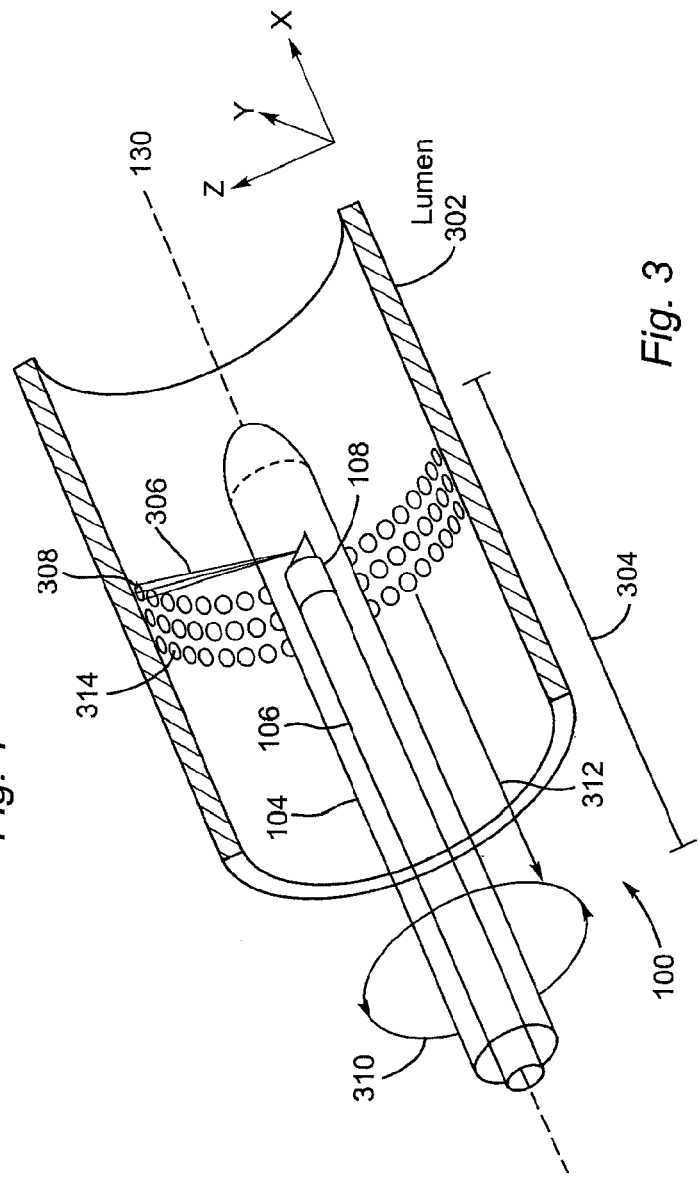
Fig. 1
Fig. 3

SYSTEMS AND METHODS FOR DYNAMIC OPTICAL IMAGING

RELATED APPLICATIONS

This application is a continuation of U.S. application Ser. No. 10/444,171, filed May 22, 2003, now U.S. Pat. No. 7,376,455, which is incorporated herewith in its entirety.

FIELD OF THE INVENTION

The field of the invention relates generally to optical imaging, and more particularly to a systems and methods for dynamic optical imaging in a medical environment.

BACKGROUND INFORMATION

The ability to image within a living body is fundamental to the proper diagnosis and treatment of medical conditions. Typically, a medical device such as a catheter or endoscope is used to gain access to and image remote regions of the body otherwise reachable only with invasive surgery. These systems use a variety of imaging techniques such as acoustical and optical imaging.

Acoustical imaging systems generally place either a phased array or single rotating transducer at the distal end of the medical device. The transducer emits acoustic pulses, i.e., mechanical sound waves, and receives the acoustic reflections that are created by the impact of these pulses with the surrounding tissues. The acoustic imaging system can then generate an image of the internal tissue based on the information provided by these reflections. The acoustic imaging system is able to produce images despite the presence of blood or other fluids surrounding the tissue. This makes acoustic imaging ideal for applications which require scanning large regions of internal tissue. For instance, when scanning internal body lumens such as blood vessels, the acoustic system can image the vessel both radially around the vessel circumference as well as longitudinally along the length of the vessel, typically referred to as "pull back." Scanning of large regions within the blood vessel can take place without seriously impeding the flow of blood.

Optical imaging systems are similar to acoustic systems in that they typically include an optical imager at the distal end of the medical device. However, optical imaging systems use the transmission and receipt of optical energy, e.g., light, to create images of tissue within the body. Optical imaging systems typically employ a type of optical coherence domain reflectometry (OCDR), such as optical coherence tomography (OCT), to generate high quality images of internal tissue. Optical imaging systems are typically faster than acoustic imaging systems and can provide a higher degree of resolution. However, because optical imaging is dependent on the propagation of light, the presence of fluids or materials that impede light propagation can prevent proper imaging. For instance, when an optical imaging system is used to image the interior of a blood vessel, the flow of blood through that vessel must be sequestered, either by introducing saline to dilate the blood within the vessel or by stopping the flow of blood altogether. Sequestration for extended periods of time, in some case for less than sixty seconds, starves the tissue of oxygen and can result in serious adverse effects and is not desired. Because optical systems require obstruction of blood flow, they can only scan for limited periods of time and accordingly, optical imaging systems are not suited for scanning large regions of tissue in a safe manner.

Thus, there is a need for improved systems and methods of imaging internal tissue.

SUMMARY

An improved medical system preferably includes a catheter and an imaging system and is configured to dynamically image large regions of body tissue in a short time period.

Described next is an example embodiment of a method of optically imaging with an improved medical device. First, a substantially transparent fluid is introduced to a body lumen with an elongated tubular member. Then, a wide band light pulse is generated from a light source and the light pulse is split into a tissue pulse and a reference pulse. The tissue pulse is then directed towards a first location of the body lumen or other body tissue with an imager and a reflected tissue pulse is received from the body lumen at the imager. Next, the reflected tissue pulse is mixed with the reference pulse in a time gate to generate a light wave corresponding to a temporal duration of the reference pulse and a spatial profile of the tissue pulse, and the light wave is detected with a plurality of detectors. Finally, the inner core is preferably radially rotated around a center axis and axially translated along the center axis to image a second location of the body lumen.

In another example embodiment, the improved medical system includes a catheter having a proximal and a distal end, the distal end insertable into a living body and configured to optically image a body lumen. The catheter includes an elongated tubular member including an opening for introducing a fluid to the body lumen and an inner core configured to slide within the elongated member. The system also preferably includes a control system configured to rotate the inner core within the elongated member radially around a center axis and also configured to translate the inner core axially along the center axis, as well as a light source optically coupled with the inner core and configured to generate a wide band light pulse. The system further includes an interferometric optical imaging system optically coupled with the array and the inner core and configured to split the light pulse into a tissue pulse and a reference pulse, wherein the inner core is configured to direct the tissue pulse towards a body lumen. The imaging system includes a time gate configured to mix a tissue pulse reflected from the body lumen with the reference pulse and output a light wave corresponding to a temporal duration of the reference pulse, and a spatial profile of the reflected tissue pulse, and also an imager comprising a plurality of light detectors configured to detect the light wave.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1 is a schematic diagram depicting an example embodiment of a medical system.

FIG. 3 is a perspective view of another example embodiment of a catheter within the medical system.

DETAILED DESCRIPTION

Figure 2:
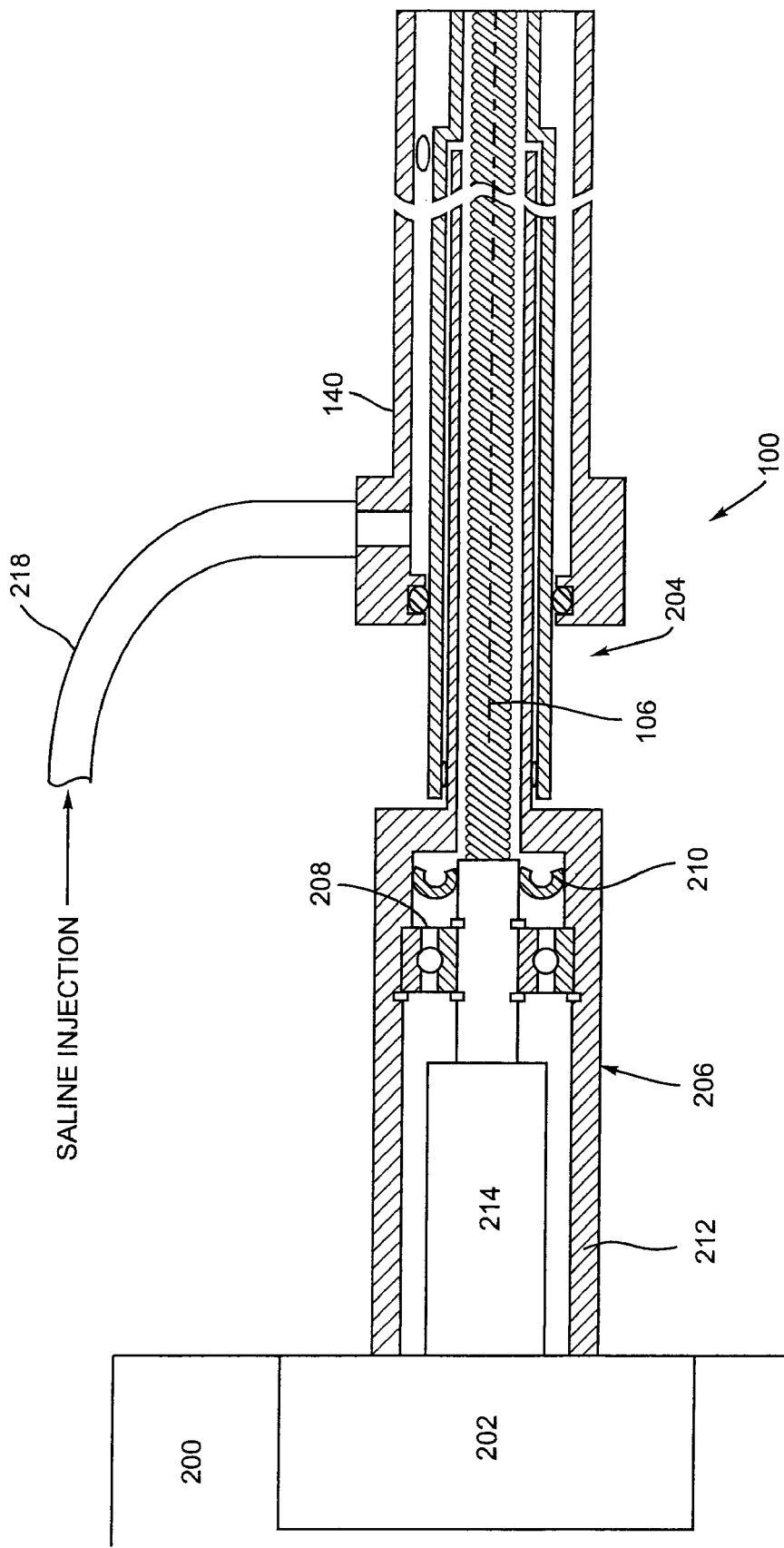
FIG. 2 is a schematic diagram depicting an example embodiment of a medical system.

The systems and methods described herein provide for the dynamic optical imaging of a body lumen or other body tissue inside a living body. In a preferred embodiment, a medical device, such as catheter, is inserted into a living body and used to image a body lumen at a high speed. For the sake of convenience, reference is made to the example embodiment of a catheter; however, such catheter embodiments can be adapted to be non-catheter embodiments. The catheter optically images the lumen at a rate high enough to allow high quality imaging of large regions of body tissue in a short period of time. These regions can be dynamically imaged in a safe manner, i.e., without the introduction of large amounts of blood-displacing fluids that can have serious adverse effects on the recipient.

FIG. 1 depicts medical system 100, which is a preferred embodiment of the systems and methods described herein. This embodiment includes medical device 102, which is preferably a catheter, elongated tubular member 104 and inner core 106. Catheter 102 includes distal end 103 and is insertable into a living body and can be advanced through a body lumen such as a blood vessel, artery, or a body canal, while at the same time imaging that body lumen or canal. Optical imager 108 is located at or near the distal end of inner core 106. Inner core 106 is slideably received within elongated member 104 and can be rotated radially around center axis 130 as well as translated axially along center axis 130. In order to image the lumen, any fluids that do not allow sufficient propagation of light, e.g., blood, are preferably displaced or sequestered prior to imaging. However, as will be seen, the improved systems require blood displacement for a shorter duration. In this embodiment, elongated member 104 includes openings 110 for introducing a substantially transparent fluid to displace any blood present in the lumen. This substantially transparent fluid is preferably saline, however any fluid can be used that allows the propagation of a sufficient amount of light to properly image the lumen according to the needs of the individual application. This method of displacing fluid while imaging a body lumen both axially and radially allows the generation of a three-dimensional image of the circumference and length of the body lumen.

Inner core 106 includes flexible drive shaft 112 that is configured to rotate optical imager 108 in a manner which is well known in the art. Inner core 106 also includes an optical signal line (not shown) that is preferably housed within the drive shaft 112 and optically couples imager 108 with imaging system 200. FIG. 2 depicts another embodiment of medical system 100, including imaging system 200, control system 202 and proximal end 204 of catheter 102. Imaging system 200 is preferably an optical coherence tomography (OCT) imaging system but can also be an optical coherence domain reflectometry (OCDR) system or any optical imaging system that allows for high speed imaging. Imaging system 200 processes the optical information contained in an optical signal reflected by the body lumen and received by imager 108. Control system 202 includes hardware and software for controlling the movement of inner core 106. More specifically, control system 202 preferably includes drive system 206 for mechanically driving the rotation and axial translation, or pull back, of inner core 106 within elongated member 104. The operation and functionality of these various systems is discussed in more detail below. Also depicted in each figure is guiding catheter 140, which is optionally used to facilitate the introduction of catheter 102 into the body lumen. Guiding catheter 140 can also be used to introduce saline into the body lumen.

A detailed description of medical system 100 is facilitated by a discussion of several example applications in which system 100 can be implemented. FIG. 3 depicts system 100 in one such example application. More specifically, FIG. 3 illustrates distal end 103 of catheter 102 inserted within a cutaway of body lumen 302. In this embodiment, system 100 scans the circumference of lumen 302 over pre-determined length 304. Imager 108 directs tissue pulse 306 towards body lumen 302 and impacts a first location at the surface of body lumen 302 forming circular cross-section 308. In order to provide better illustration of this embodiment, the size of cross-section 308 has been exaggerated in FIG. 3. Tissue pulse 306 penetrates body tissue 302 and reflects back to imager 108 and is communicated to imaging system 200. The information in the reflected signal is used to generate a two-dimensional image of the depth, in the z-direction, and the length, in the x-direction, of lumen 302.

Inner core 106 then rotates radially in direction 310, the y-direction, and translates, or moves, axially along axis 130 in direction 312 to a second location on lumen 302. A second tissue pulse 306 is directed to the second location and the information in the reflected signal is communicated to imaging system 200 and the process repeats until the circumference of lumen 302 is imaged along length 304. The images taken at the consecutive locations can be combined together to form a three-dimensional image of lumen 302. Throughout the imaging process any blood present in lumen 302 is either sequestered or displaced by the infusion of saline from opening 110.

In one example embodiment, length 304 is 50 millimeters (mm) and saline is infused at a rate of 4 cubic centimeters (cc) per second (sec). As in any optical imaging application, care must be taken to avoid harm to the recipient from excessive amounts of saline infusion. For a typical recipient, a safe amount of saline that does not result in significant harm is approximately 30 cubic centimeters. As one of skill in the art will readily realize this safe level varies with the recipient's body characteristics. To maintain patient safety by limiting the level of saline infusion to an acceptable level, length 304 is preferably imaged in 8 seconds. This is a pull back rate of 6.25 mm/sec and results in a tolerable total saline infusion of 32 cubic centimeters.

Typical optical imaging systems radially rotate at a low rate of 26 revolutions every second, with either 256 or 512 separate imaging locations 314, referred to as vectors, in one complete circumference of lumen 302. The set of vectors imaged in one circumference of lumen 302 is referred to as an imaging plane. Because of this low rotational speed, the typical imaging system cannot image any significant length of lumen 302 without infusing dangerously high amounts of saline and, therefore, these systems operate at a low translational speed or do not translate at all. As will be demonstrated in the following example embodiment, optical imaging system 100 is capable of operating at both a relatively higher rotational speed and a relatively higher translational speed than the typical imaging system, allowing optical imaging system 100 to image while maintaining patient safety.

In this example embodiment, the distance between imager 108 and lumen 302 is 1 mm and the angle between vectors 314 is 0.7 degrees, resulting in a distance between vectors 314 of 0.012 mm, with 512 vectors in one imaging plane. Preferably, the distance between two consecutive imaging planes, or pitch, is approximately equal to the distance between two consecutive vectors 314, resulting in a pitch of 0.012 mm/rev. In addition, the distances can be adjusted to allow overlap between adjacent cross-sections 308. Overlap between vectors 314 allows higher degrees of resolution and accuracy. To achieve a rate of pull back of 6.25 mm and a pitch of 0.012 mm, the rate of rotation is preferably 520 revolutions per second (rev/sec), or 31200 revolutions per minute (rpm). This can be determined by taking rate of pull back and dividing it by the pitch between imaging planes. A rate of 520 rev/sec with 512 vectors per revolution results in a processing speed of 266240 vectors/sec (520 rev/sec*512 vectors/rev).

A second example can be given to illustrate operation of system 100 at an even higher speed. In this example embodiment, in order to further limit the total amount of saline infusion, scanning of length 304 takes place in 4 seconds, at a pull back rate of 12.5 mm/sec. With the same pitch as the previous example, the rotational rate of inner core 106 is 1040 rev/sec, or 12.5 mm/sec divided by 0.012 mm/rev. With 512 vectors 314 per revolution, system 100 processes at a rate of 532480 vectors/sec, or twice as fast as the example embodiment depicted above.

These two examples serve to illustrate the relation between length 304, scanning time, lumen size, pitch and the number of vectors 314 in an individual rotation. These values will vary depending on the size of lumen 302 and the needs of each particular application. For example, a shorter length 304 than 50 mm would in turn allow more vectors 314 per revolution, a lower pitch between revolutions, or a lower revolution rate in order to maintain the same processing speed. One of skill in the art will readily recognize the interrelation between these variables and the effects a modification of one would have on the others. Accordingly, the systems and methods described herein are not limited to any one example embodiment and can be adjusted and configured according to the needs of each individual application.

In a preferred embodiment, each revolution of inner core 106 produces one frame resulting in a frame rate of 520 per second. Each frame is preferably stored in a memory to allow viewing at any rate. Since a typical human perceives motion at a viewing rate of approximately 30-35 frames/sec, imaging system 200 can be configured to display these frames from memory at a rate equal or near this basic viewing rate. However the frames can be viewed in real-time (520 frames/sec) or any other desired rate according to the needs of the individual application. At a frame rate of 32 frames/sec, the viewing of the scanned frames from length 304 would take approximately 130 seconds.

Referring back to FIG. 2, imaging system 200 is optically coupled with proximal end 204 of catheter 102 through drive system 206. Control system 202 controls the operation of drive system 206 including the rotation and translation rates of inner core 106. Drive system 206 includes housing 212 and rotary joint 214. In order to allow the dynamic high speed operation of system 100, drive system 206 preferably includes one or more high speed ball bearings 208 and one or more high speed seals 210. Bearings 208 are preferably retractably coupled between rotary joint 214 and housing 212 and are configured to rotate at the rate required by the individual application. For instance, in an embodiment capable of performing in the range of speeds demonstrated in the above two examples, bearings capable of rotating in the approximate range of 30,000 to 65,000 rpm are preferably used. In addition, high speed seals 210 can also used to prevent saline or other infusion fluids from escaping from within member 104 into drive system 206.

In another embodiment of system 100, a lubricant, such as a silicone-based lubricant, is placed in the space between elongated member 104 and inner core 106 to combat the friction effects resulting from the high rotational rate within catheter 102. In an example embodiment, the diameter of inner core 106 is approximately 0.6 mm for a 3 french catheter 102, which translates into 1.9 mm of circumference and a relative speed of approximately 1 meter/sec at a rotational rate of 520 rev/sec and 2 meters/sec at a rotational rate of 1040 rev/sec. These rates can result in significant friction, especially as the rotational rate increases or the diameter of inner core 106 increases. In addition, to combat friction, the space between member 104 and inner core 106, i.e., the difference between the respective diameters, can be enlarged to reduce the amount of contact between member 104 and inner core 106. In this embodiment, a separate lumen is contained within member 104 and connects flush port 218 with opening 110 in order to allow saline to be infused without mixing with lubricant.

Figure 4:
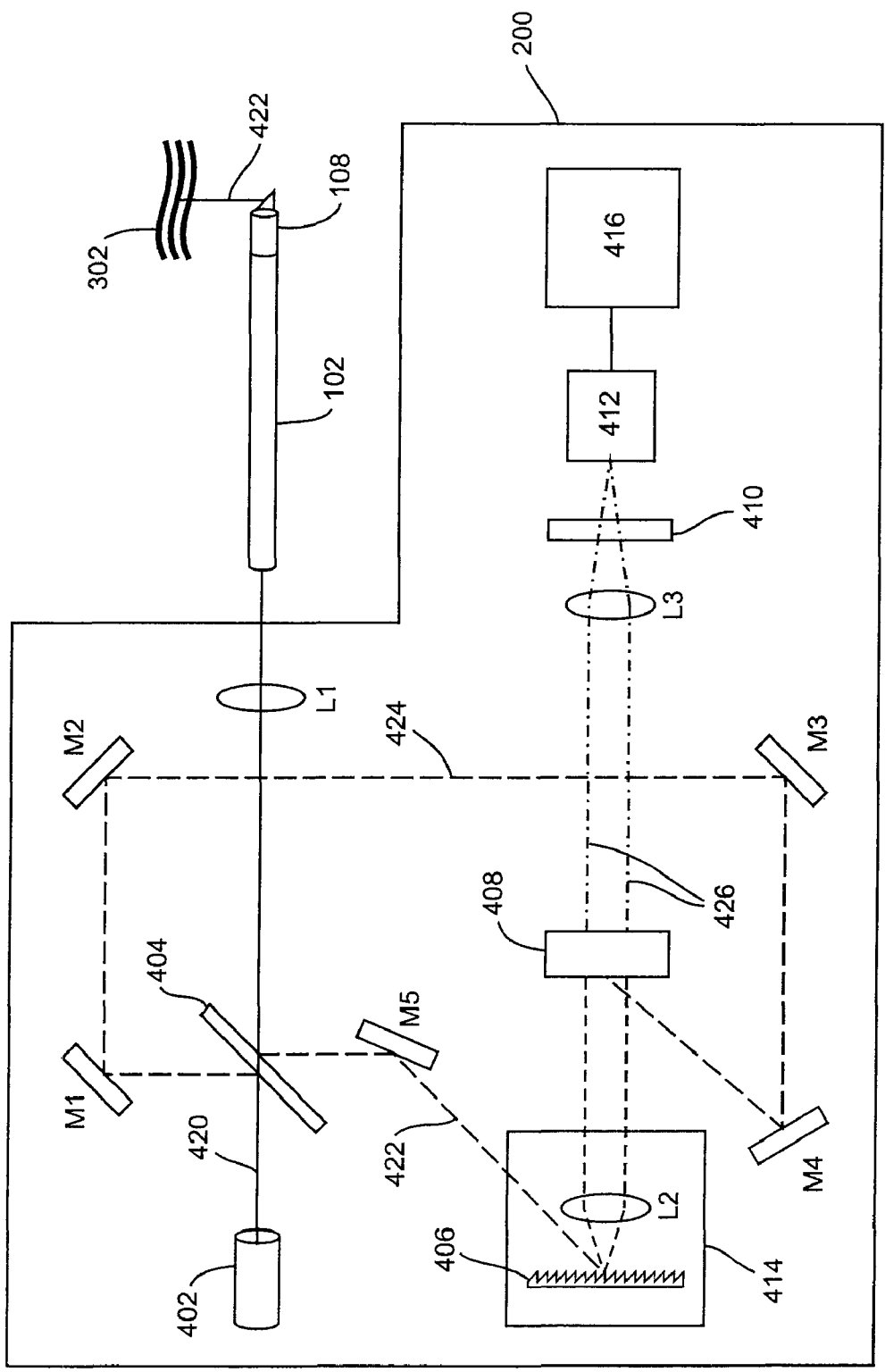
FIG. 4 is a schematic diagram depicting another example embodiment of a medical system.

FIG. 4 depicts an example embodiment of imaging system 200 and catheter 102 configured to image lumen 302 at high speed. In this embodiment, imaging system 200 is an interferometric OCT imaging system; however, system 200 is not limited to this form of OCT imaging and can be used with any imaging technique that allows for high speed imaging. Interferometric imaging system 200 includes wide band light source 402, beam splitter 404, diffraction grating 406, mixer 408, filter 410 and detection array 412. System 200 allows the generation of a three-dimensional image of lumen 302 with only one-dimensional scanning, through the use of parallel processing and time gating. The use of time gating has been discussed in detail in Yasuno, et al., *Spectral Interferometric Optical Coherence Tomography with Nonlinear β-Barium Borate Time Gating*, Optics Letters, Vol. 27, No. 6, Mar. 15, 2002, and the use of parallel processing has been discussed in Zeylikovich et al., System and Method for Performing Selected Optical Measurements on a Sample Using a Diffraction Grating, U.S. Pat. No. 5,943,133, both of which are expressly incorporated by reference herein.

Wide band light source 402 generates wide band light beam pulse 420 and directs it towards beam splitter 404, which, in this embodiment, is a 50/50 beam splitter. Beam splitter 404 splits beam 420 in two, generating tissue pulse 422 and reference pulse 424. One of skill in the art will readily recognize that interferometric OCT systems can be implemented with various beam splitting ratios and accordingly, system 100 is not limited to any one ratio of beam splitting. Light source 402 preferably generates light beam 420 in a pulsed manner to allow imaging with high intensity light without significant risk of tissue damage. The reduction in duty cycle of the beam reduces the total energy delivered to the body yet still allows high intensity which is preferably timed to coincide with the acquisition of the reflected pulse. Powering pulsed superluminescent diodes (SLD's) or lasers preferably requires processing system 416 to generate a timing signal to trigger a discharge type power supply (not shown) and is well known to one of skill in the art. However, light source 402 is not limited to a pulsed source and can be delivered in a continuous wave format if the characteristics of system 100, including the signal-to-noise ratio, are such as to allow the use of a lower intensity continuous source.

Light beam pulse 420 has a wide bandwidth which is indirectly proportional to the coherence length of the beam and accordingly, allows for higher imaging resolution. Light source 402 can be any wide band pulsed light source, including a short pulse laser or an SLD. Also, source 402 can be implemented as an array of multiple SLD's to allow for a wider bandwidth. These embodiments will be discussed in more detail below.

For ease of illustration, light beams are depicted as being directed through free space, however, in a preferred embodiment these light beams are directed with the aid of an optical channel such as a fiber optic. The use of fiber optics can also eliminate the use of mirrors for directing the light pathway. Tissue pulse 422 is directed through lens L1 and into inner core 106 to imager 108, which in turn directs pulse 422 onto lumen 302. Lens L1 focuses pulse 422 in one spatial direction into body lumen or other body tissue 302. Tissue pulse 422 penetrates lumen 302 and is modulated, or reflected and backscattered, from multiple points within lumen 302. Imager 108 receives this reflected tissue pulse 422 and directs it back to beam splitter 404 through inner core 106. Reflected tissue pulse 422 contains the spatial and temporal profiles of lumen 302, where the depth information is contained within the temporal profile. Beam splitter 404 then directs reflected pulse 422 towards spectrometer 414, including diffraction grating 406 and lens L2.

One of skill in the art will readily recognize the existence of numerous different spectrometer configurations that can be used in interferometric OCT imaging. In this embodiment, diffraction grating 406 and lens L2 spatially decompose reflected tissue pulse 422 into temporal spectral components which are directed onto mixer 408. Mixer 408 can be any mixer or device capable of mixing, or combining, multiple light pulses and outputting the mixed light pulse. In a preferred embodiment, mixer 408 is a time gate configured to accept reflected pulse 422 and reference pulse 424 and output a light wave 426 corresponding to the temporal duration of reference pulse 424 and having substantially the same spatial profile as reflected pulse 422.

Time gate 408 is used to cancel any phase skew in reflected pulse 422. This phase skew occurs as a result of the modulation and diffraction of pulse 422, as well as the temporal duration of pulse 422, which, for instance, can be in the range of several picoseconds and can cause spatial signal shifting on detection array 412. A delay line (not shown) is used to adjust the flight time of reference pulse 424 which is also directed onto time gate 408 by multiple mirrors M1-M5. In this embodiment, time gate 408 is a nonlinear β-barium borate time gate crystal and is used to mix the incident tissue pulse 422 and reference pulse 424 to generate light wave 426. Light wave 426 is preferably a harmonic wave that corresponds to the temporal duration of the reference pulse 424, which, in this embodiment, is approximately 150 femtoseconds (fs). Harmonic wave 426 has the same spatial profile as tissue pulse 422 with a shorter duration corresponding to reference pulse 424 and significantly reduces the phase skew of the incident tissue pulse 422. In one embodiment, time gate 408 is triggered by reference pulse 424 and mixes tissue pulse 422 and reference pulse 424 upon incidence by reference pulse 424 on time gate 408.

The depth structure of lumen 302 is then Fourier transformed by lens L3 and spatially projected through filter 410 onto detection array 412. Filter 410 is preferably a bandpass filter and is used to eliminate noise and interference components outside harmonic wave 426. Detection array 412 is an array of light detectors such as a charge-coupled device or semiconductor-based imager that is capable of detecting the light intensity of harmonic wave 426 during the short duration of incidence on array 412. Array 412 preferably includes a sufficient number of light detectors to detect all diffracted portions of reflected tissue pulse 422 with a degree of resolution suitable for the needs of the application. Array 412 is communicatively coupled with processing system 416, which is configured to process the projected depth structure and assemble the two and three-dimensional images in a viewable format. Processing system 416 is preferably a computer, but can be any customized or standard data processing system with sufficient capability to process the images at a rate determined by the needs of the individual application.

In some embodiments, the high imaging and acquisition speed of system 100 can result in more noise throughout the system, and can result in a decreased signal-to-noise ratio (SNR). In one preferred embodiment, the signal strength or intensity, of light source 402 is increased in order to compensate for higher noise levels, such as by implementing light source 402 as an SLD array including two or more superluminescent diodes. In one embodiment, source 402 is two arrayed SLD's with offset center bandwidths. After imaging, processing system 416 algorithmically fits the spectral density of arrayed source 402 into a gaussian distribution, effectively creating a gaussian, high intensity, wide beam source. This spectral shaping technique allows system 100 to raise the signal strength of source 402 and widen the bandwidth of source 402 and in turn increase the SNR without losing resolution and accuracy resulting from a non-gaussian spectral density. Spectral shaping is discussed in detail in Tripathi et al., *Spectral Shaping for non-Gaussian Source Spectra in Optical Coherence Tomography*, Optics Letters, Vol. 27, No. 6, Mar. 15, 2002, which is expressly incorporated by reference herein. The implementation of this spectral shaping technique in combination with the embodiment of imaging system 200 depicted in FIG. 4 can allow high speed imaging with an increased SNR.

In this embodiment, the combined spectral densities of the two SLD's is calculated by Fourier transforming the interferometric responses of a tissue pulse to a single surface, such as a mirror or glass slide. This combined spectral density can be stored in memory within processing system 416. Then, the spectral density is determined from an image created by the incident harmonic wave 426 by calculating the average square root of the power spectrum. An ideal gaussian source spectrum can then be determined by preferably using the zeroth moment of the spectral density obtained from the lumen response and the first and second moments of the spectral density obtained from the single surface response. The ratio of the ideal gaussian source spectrum and the measured source spectrum defines a spectral correction curve. Multiplying the Fourier transform of each individual image by the spectral correction curve gives the spectrally filtered gaussian response of each image. The coherence function envelope can then be obtained through digital quadrature demodulation.

In this embodiment, the gaussian coherence function of non-gaussian source 402 can be obtained by Fourier transforming harmonic wave 426, applying a correction to each Fourier component and inverse transforming the corrected signal. The signal processing algorithm for this spectral shaping technique is preferably stored and performed in processing system 416. Preferably, the SLD's implemented in source 402 are orthogonally polarized and can be combined using a polarizing beam splitter. Therefore, the improved systems reduce the duration of blood displacement and can create 3D images from an interior body scan.

In addition to the embodiments described herein, system 100 can be used in conjunction with other features known in the art, such as additional guiding catheters, guidewires and prostheses, including inflatable balloons and stents. Furthermore, the length and composition of catheter 102 and the constituent components varies on the needs of the individual application. Elongated member 104 can be made from any suitable material or combination of materials including Pebax 70A, Tecoflex, polyethylene, nylon, hypo-tube, natural rubber, silicone rubber, polyvinylchloride, polyurethanes, polyesters, polytetrafluorothylene (PTFE), and thermoplastic polymers. It can also be formed as a composite having a reinforcement material incorporated within catheter 102 in order to enhance strength, flexibility, and toughness. Suitable enforcement layers include wire mesh layers and the like.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving high speed optical imaging in a catheter, but can be used in any design involving optical imaging. As a further example, each feature of one embodiment can be mixed and matched with other features shown in other embodiments. Features and processes known to those of ordinary skill in the art of optical imaging may similarly be incorporated as desired. Additionally and obviously, features may be added or subtracted as desired. Accordingly, the invention is not to be restricted except in light of the attached claims and their equivalents.

What is claimed is:

1. A system, comprising:
   a catheter having a proximal and a distal end, the distal end insertable into a living body and configured to optically image a body tissue, comprising:
      an elongated tubular member comprising an opening for introducing a fluid to the body tissue; and
      an inner core configured to slide within the elongated member;
   a control system configured to rotate the inner core within the elongated member radially around a center axis and configured to translate the inner core axially along the center axis; and
   an optical imaging system coupled to the inner core, wherein the optical imaging system is configured to acquire optical images from the inner core at a rate greater than or substantially equal to 520 frames per second;
   wherein the control system is configured to axially translate the inner core at a rate greater than or substantially equal to 6.25 millimeters per second while acquiring the optical images.

2. The system of claim 1, wherein the control system is configured to rotate the inner core at a rate greater than or substantially equal to 520 revolutions per second while acquiring the optical images.

3. The system of claim 1, wherein the imaging system is further configured to generate a three-dimensional image of the body tissue.

4. The system of claim 1, further comprising a lubricant disposed in the region between the inner core and the elongated member.

5. The system of claim 1, wherein the imaging system is configured to image substantially 256 separate locations of the body tissue in one revolution.

6. The system of claim 1, wherein the control system controls a drive system configured to radially rotate and axially, the drive system comprising:
   a housing;
   a rotary joint located within the housing and coupled with a proximal end of the inner core;
   a high speed ball bearing rotatably coupled with the rotary joint and the housing; and
   a high speed seal located distal to the bearing and configured to seal the housing from an interior space of the elongated member.

7. The system of claim 6, wherein the high speed ball bearing is configured to rotate at a rate of between 30,000 and 65,000 rpm.

8. The system of claim 1, wherein the catheter comprises a flush port at the proximal end, the flush port configured to introduce the fluid into an interior space of the elongated member, wherein the fluid is introduced to the body tissue through the opening.

9. The system of claim 8, wherein the flush port is configured to introduce fluid at a rate less than or substantially equal to 4 cubic centimeters per second.

10. The system of claim 8 wherein the fluid is substantially transparent.

11. The system of claim 10, wherein the fluid is saline.

12. The system of claim 1, wherein the imaging system comprises:
   a light source optically coupled with the inner core and configured to generate a wide band light pulse; and
   an interferometric optical system optically coupled with the light source and the inner core and configured to split the light pulse into a tissue pulse and a reference pulse, wherein the inner core is configured to direct the tissue pulse towards the body tissue, the interferometric optical system comprising:
      a mixer configured to mix a tissue pulse reflected from the body tissue with the reference pulse and output a light wave corresponding to a temporal duration of the reference pulse and a spatial profile of the reflected tissue pulse;
      an imager comprising a plurality of light detectors configured to detect the light wave, wherein the imager is configured to acquire images from the inner core at a frame rate of at least 520 frames per second; and
      a lens configured to spatially project a depth structure of the body tissue from the light wave onto the plurality of the light detectors.

13. The system of claim 12, wherein the interferometric optical system is further configured to algorithmically shape a non-gaussian spectral density of the light wave to create a gaussian spectral density.

14. The system of claim 12, wherein the light source comprises a plurality of superluminescent diodes.

15. The system of claim 12, wherein the imager comprises a charge-coupled device.

16. A method of optically imaging a body tissue, comprising:
   introducing a substantially transparent fluid to a body tissue with an elongated tubular member;
   radially rotating an inner core around a center axis within the elongated tubular member, wherein the inner core includes an optical imager;
   axially translating the inner core along the center axis within the elongated tube at a rate greater than or substantially equal to 6.25 millimeters per second; and acquiring optical images at a frame rate of at least 520 frames per second from the inner core as the inner core is translated axially.

17. The method of claim 16, wherein the inner core is rotated at a rate of at least 520 revolutions per second while acquiring the optical images.

18. The method of claim 16, further comprising radially rotating the inner core to image 512 separate locations of the body tissue in one revolution of the inner core.

19. The method of claim 16, wherein the introducing of the fluid introduces the fluid at a rate less than or substantially equal to 4 cubic centimeters per second.

20. The method of claim 16, further comprising:
generating a wide band light pulse from a light source;
splitting the light pulse into a tissue pulse and a reference pulse;
directing the tissue pulse towards a first location of the body tissue with the imager located on the inner core within the elongated member;
receiving a reflected tissue pulse from the body tissue with the imager;
mixing the reflected tissue pulse with the reference pulse in a mixer to generate a light wave corresponding to a temporal duration of the reference pulse and a spatial profile of the tissue pulse;
spatially projecting a depth structure of the body tissue from the light wave onto a plurality of the light detectors; and
detecting the light wave with the plurality of detectors.

21. The method of claim 20, wherein directing the tissue pulse towards a first location comprises directing the tissue pulse with an optical imager located on a distal end of the inner core.

22. The method of claim 20, further comprising generating an image of the first location from the detected light wave prior to rotating the inner core.

23. The method of claim 22, further comprising generating an image of a second location and combining the image of the second location with the image of the first location to form a three-dimensional image of the body tissue.

24. The method of claim 22, further comprising algorithmically shaping a non-gaussian spectral density of the light wave to create a gaussian spectral density.

25. The method of claim 24, wherein generating a wide band light pulse includes using a plurality of superluminescent diodes.

26. The method of claim 22, further comprising storing the image of the first location.

27. The method of claim 26, further comprising viewing the stored images at a pre-determined rate.

\* \* \* \* \*